United States Patent
Suzuki et al.

(10) Patent No.: US 9,687,474 B2
(45) Date of Patent: *Jun. 27, 2017

(54) PATCH

(71) Applicant: HISAMITSU PHARMACEUTICAL CO., INC., Tosu-shi (JP)

(72) Inventors: Masayuki Suzuki, Tsukuba (JP); Hiroaki Okutsu, Tsukuba (JP); Takashi Yasukochi, Tsukuba (JP); Yasunori Takada, Tsukuba (JP)

(73) Assignee: HISAMITSU PHARMACEUTICAL CO., INC., Tosu-shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/416,964

(22) PCT Filed: Jul. 25, 2013

(86) PCT No.: PCT/JP2013/070196

§ 371 (c)(1),
(2) Date: Jan. 23, 2015

(87) PCT Pub. No.: WO2014/017594

PCT Pub. Date: Jan. 30, 2014

(65) Prior Publication Data

US 2015/0202183 A1    Jul. 23, 2015

(30) Foreign Application Priority Data

Jul. 26, 2012 (JP) .................. 2012-165793
Apr. 4, 2013 (JP) .................. 2013-078583

(51) Int. Cl.

| A61K 31/407 | (2006.01) |
|---|---|
| A61K 47/14 | (2017.01) |
| A61K 47/10 | (2017.01) |
| A61K 9/70 | (2006.01) |
| A61K 47/06 | (2006.01) |
| A61K 47/12 | (2006.01) |

(52) U.S. Cl.
CPC .......... *A61K 31/407* (2013.01); *A61K 9/7038* (2013.01); *A61K 9/7046* (2013.01); *A61K 9/7053* (2013.01); *A61K 9/7061* (2013.01); *A61K 9/7069* (2013.01); *A61K 47/06* (2013.01); *A61K 47/10* (2013.01); *A61K 47/12* (2013.01); *A61K 47/14* (2013.01)

(58) Field of Classification Search
CPC .. C12N 1/20; C12R 1/19; A61K 35/74; A61K 31/407; A61K 47/10; A61K 47/06; A61K 9/7053; A61K 9/7046; A61K 9/7061; A61K 9/7069; A61K 9/7038; A61K 47/14; A61K 47/12

See application file for complete search history.

(56) References Cited

U.S. PATENT DOCUMENTS

| 4,740,374 A | 4/1988 | Nakano et al. |
|---|---|---|
| 7,504,114 B1 | 3/2009 | Kurita et al. |
| 2004/0142024 A1 | 7/2004 | Chono et al. |
| 2007/0184097 A1 | 8/2007 | Kurita et al. |
| 2011/0189261 A1 | 8/2011 | Kuribayashi et al. |

FOREIGN PATENT DOCUMENTS

| EP | 1 201 232 A1 | 5/2002 |
|---|---|---|
| JP | 62-126119 A | 6/1987 |
| JP | 01-207246 A | 8/1989 |
| JP | 10-251145 A | 9/1998 |
| JP | 11-302161 A | 11/1999 |
| JP | 2008-100939 A | 5/2008 |
| WO | WO 00/61120 A1 | 10/2000 |
| WO | 01/07018 A1 | 2/2001 |
| WO | 2005/115355 A1 | 12/2005 |
| WO | 2009/110351 A1 | 9/2009 |
| WO | 2010/127674 A1 | 11/2010 |
| WO | 2011/136283 A1 | 11/2011 |

OTHER PUBLICATIONS

International Search Report issued Sep. 10, 2013 in PCT/JP2013/070195.
International Preliminary Report on Patentability and Written Opinion issued Feb. 5, 2015 in PCT/JP2013/070196 (English translation only).
International Search Report issued Sep. 10, 2013 in PCT/JP2013/070196 filed Jul. 25, 2013.
Hong Guo, et al. "Effects of Isopropyl Palmitate on the Skin Permeation of Drugs" Biol. Pharm. Bull, vol. 29, No. 11, 2006, pp. 2324-2326.
Extended European Search Report issued on Feb. 5, 2016 in Patent Application No. 13822503.2.
Raymond C. Rowe, et al., "Isopropyl Palmitate", Pharmaceutical Excipients, XP002666039, 2011, pp. 1-4.
U.S. Appl. No. 14/417,205, Jan. 26, 2015, Suzuki, et al.

Primary Examiner — John Pak
Assistant Examiner — Andriae M Holt
(74) Attorney, Agent, or Firm — Oblon, McClelland, Maier & Neustadt, L.L.P.

(57) ABSTRACT

In a patch comprising a support layer and an adhesive agent layer, the adhesive agent layer comprises asenapine and/or a pharmaceutically acceptable salt thereof, isopropyl palmitate, and an adhesive base agent.

17 Claims, 1 Drawing Sheet

PATCH

TECHNICAL FIELD

The present invention relates to a patch. Specifically, the present invention relates to a patch using asenapine as a drug.

BACKGROUND ART

Asenapine (trans-5-chloro-2-methyl-2,3,3a,12b-tetrahydro-1H-dibenz[2,3:6,7]oxepino[4,5-c]pyrrole) is a compound having a central nervous system (CNS)-suppressing activity, an anti-histamine activity, and an anti-serotoninergic activity. Asenapine is known as a drug for use in the treatment of central nervous system diseases such as schizophrenia.

For example, International Publication No. WO2010/127674 (PTL 1) describes pharmaceutical preparations containing asenapine, in the form of topical agents such as sprays, aerosols, patches, and ointments. Moreover, International Publication No. WO2011/136283 (PTL 2) describes a transdermal preparation containing a skin irritation suppressant including a cholesterol compound, a drug, and a pharmaceutical ingredient. PTL 2 cites asenapine as the drug, and also cites lauric acid diethanolamine, propylene glycol monolaurate, and sorbitan monolaurate as the pharmaceutical ingredient. However, such conventional pharmaceutical preparations containing asenapine have a problem that an adverse effect is likely to occur. In addition, particularly, such topical agents have a problem that it is difficult to keep the plasma concentration of asenapine at a therapeutically effective level.

On the other hand, heretofore, various patches have been developed in order to improve the skin permeability of a drug contained in the patches. For example, International Publication No. WO01/07018 (PTL3) discloses a patch containing a basic drug, an organic acid, and an organic acid salt. PTL 3 discloses acetic acid, lactic acid, and the like as the organic acid, and sodium acetate and the like as the organic acid salt. Further, for example, International Publication No. WO2005/115355 (PTL 4) discloses that a patch containing a basic drug and a volatile organic acid further contains an organic acid salt. Furthermore, PTLs 3 and 4 state that the patches may further contain an absorption enhancer (permeation enhancer), and cite various compounds as the absorption enhancer, such as lauryl alcohol, 1-menthol, propylene glycol, pirotiodecane, sorbitan monolaurate, isostearyl alcohol, lauric acid diethanolamide, propylene glycol monolaurate, glycerin monolaurate, lauric acid, and isopropyl myristate.

CITATION LIST

Patent Literature

[PTL 1] International Publication No. WO2010/127674
[PTL 2] International Publication No. WO2011/136283
[PTL 3] International Publication No. WO01/07018
[PTL 4] International Publication No. WO2005/115355

SUMMARY OF INVENTION

Technical Problems

However, the cited literatures 3 and 4 do not disclose at all a patch using asenapine as a drug. Meanwhile, the present inventors have found that when a pharmaceutical preparation containing asenapine is administered, increasing the amount of asenapine shifted into plasma, in other words, the area under plasma concentration-time curve (AUC) of free asenapine, also increases the amount of an asenapine metabolite in the plasma (the AUC of the asenapine metabolite), so that the incidence proportion of adverse effects is increased.

The present invention has been made in view of the problems of the conventional techniques, and an object of the present invention is to provide a patch capable of achieving a therapeutically effective level of plasma concentration of asenapine which is sufficiently higher than ever achieved, and also capable of sufficiently suppressing the plasma concentration of an asenapine metabolite.

Solution to Problems

The present inventors have conducted earnest study to achieve the above object. As a result, the inventors have found that incorporating a combination of asenapine and/or a pharmaceutically acceptable salt thereof, isopropyl palmitate, and an adhesive base agent into an adhesive agent layer of a patch comprising a support layer and the adhesive agent layer enables the skin permeability of asenapine to be sufficiently high, and makes it possible to achieve a therapeutically effective level of plasma concentration of asenapine which is sufficiently higher than ever achieved. Further, the inventors have found that administering asenapine using such a patch can sufficiently suppress the plasma concentration of an asenapine metabolite. These findings have led to the completion of the present invention.

Specifically, a patch of the present invention is a patch comprising a support layer and an adhesive agent layer, characterized in that the adhesive agent layer comprises asenapine and/or a pharmaceutically acceptable salt thereof, isopropyl palmitate, and an adhesive base agent.

Moreover, in the patch of the present invention, a mass ratio of the asenapine and/or pharmaceutically acceptable salt to the isopropyl palmitate (a mass of the asenapine and/or pharmaceutically acceptable salt in terms of free asenapine:a mass of the isopropyl palmitate) in the adhesive agent layer is preferably 1:0.1 to 1:10.

Further, in the patch of the present invention, the adhesive agent layer preferably further comprises sodium diacetate; more preferably, a mole ratio of the asenapine and/or pharmaceutically acceptable salt to the sodium diacetate (the number of moles of the asenapine and/or pharmaceutically acceptable salt:the number of moles of the sodium diacetate) in the adhesive agent layer is 1:0.5 to 1:4.

In addition, in the patch of the present invention, the adhesive base agent is preferably at least one selected from the group consisting of (meth)acrylic ester (co)polymers, rubber-based adhesive agents, silicone polymers, and polyurethane-based adhesive agents.

Furthermore, in the patch of the present invention, preferably, when a content of the asenapine and/or pharmaceutically acceptable salt in terms of free asenapine is 3.4 mg in the adhesive agent layer, an area under plasma concentration-time curve of the free asenapine between 2 and 120 hours for a period starting from the time when the patch is brought into contact with skin for 24 hours ($AUC_{2\text{-}120}$) is 27,000 pg·hr/mL or more, and an $AUC_{2-120}$ of an asenapine metabolite is 20% or less of the $AUC_{2-120}$ of the free asenapine.

Advantageous Effects of Invention

The present invention makes it possible to provide a patch capable of achieving a therapeutically effective level of plasma concentration of asenapine which is sufficiently higher than ever achieved, and also capable of sufficiently suppressing the plasma concentration of an asenapine metabolite.

DESCRIPTION OF EMBODIMENTS

Figure 1:
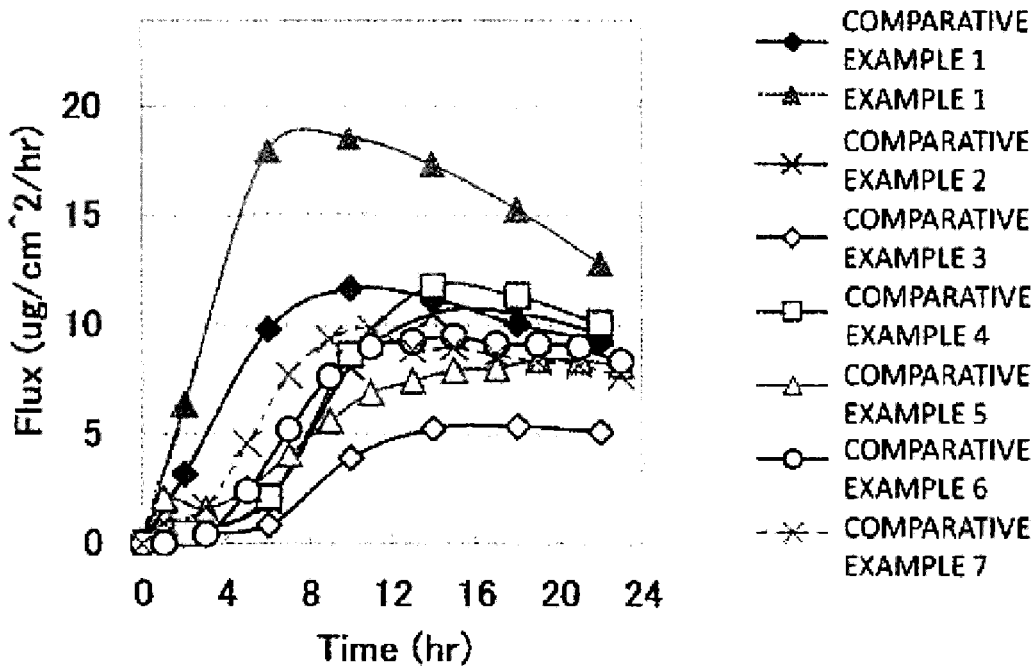
FIG. 1 is a graph showing a relation between the elapsed time from the application and skin permeation rates of asenapine in patches obtained in Example 1 and Comparative Examples 1 to 7.

Hereinafter, the present invention will be described in detail based on preferred embodiments thereof. A patch of the present invention is a patch comprising a support layer and an adhesive agent layer, characterized in that the adhesive agent layer comprises asenapine and/or a pharmaceutically acceptable salt thereof, isopropyl palmitate, and an adhesive base agent.

The patch of the present invention comprises: the support layer; and the adhesive agent layer arranged on at least one surface of the support layer. As the support layer according to the present invention, conventionally known ones can be used as appropriate. Examples of the material of such a support layer include synthetic resins such as polyethylene, polypropylene, polybutadiene, ethylene-vinyl acetate copolymers, vinyl acetate-vinyl chloride copolymers, polyvinyl chloride, polyamides such as nylons, polyesters, cellulose derivatives, and polyurethane. Moreover, examples of the form of the support layer include films; sheets; sheet-shaped porous articles; sheet-shaped foamed articles; fabrics such as woven fabrics, knitted fabrics, and nonwoven fabrics; laminates thereof; and the like. In the present invention, the thickness of the support layer is not particularly limited, but normally a preferable thickness is approximately 2 to 3000 μm.

Additionally, the patch of the present invention may further comprise a release liner on a surface of the adhesive agent layer, the surface being opposite to the support layer. The release liner only needs to be capable of covering the adhesive agent layer before the patch is used, and removable by releasing when used. Specific examples of the release liner include polyesters such as polyethylene terephthalate and polyethylene naphthalate; polyolefins such as polyethylene and polypropylene; films of polyvinyl chloride, polyvinylidene chloride, and the like; laminate films of woodfree paper and polyolefins; films of nylons, aluminium, and the like; and other similar materials. From the viewpoint of facilitating the releasing from the adhesive agent layer, these release liners used are preferably subjected to surface coating (releasing process) using a release agent such as silicone or polytetrafluoroethylene.

The adhesive agent layer according to the present invention comprises asenapine and/or a pharmaceutically acceptable salt thereof, isopropyl palmitate, and an adhesive base agent. The thickness of such an adhesive agent layer is not particularly limited, and is normally approximately 10 to 1000 μm.

<Asenapine>

The asenapine according to the present invention refers to trans-5-chloro-2-methyl-2,3,3a,12b-tetrahydro-1H-dibenz[2,3:6,7]oxepino[4,5-c]pyrrole, and is represented by the following formula (1):

[Chem. 1]

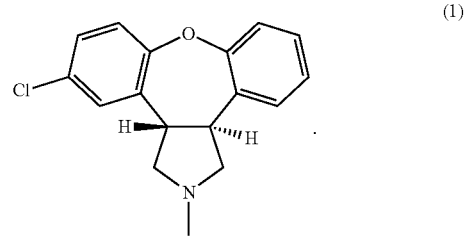

(1)

The asenapine has a central nervous system (CNS)-suppressing activity, an anti-histamine activity, and an anti-serotoninergic activity, and is normally known as a drug for use in the treatment of central nervous system diseases such as schizophrenia. Such asenapine may be in a free form, a pharmaceutically acceptable salt thereof, or a mixture of these. Nevertheless, preferable is a pharmaceutically acceptable salt of asenapine, and more preferable is a pharmaceutically acceptable acid addition salt of asenapine, from the viewpoints that the storage stability is excellent and that the change in color of the adhesive agent layer due to decomposition of asenapine is suppressed, and from the viewpoint that the irritation to skin is suppressed. Generally, the drug is preferably in a free form from the viewpoint that the skin permeability is improved. Nonetheless, in the present invention, an excellent skin permeability of asenapine is exhibited even when the asenapine is in a salt form.

Examples of an acid in the pharmaceutically acceptable acid addition salt of asenapine include monobasic acids such as hydrochloric acid, hydrobromic acid, and methanesulfonic acid; and polybasic acids such as fumaric acid, maleic acid, citric acid, and tartaric acid. Among these, preferable is hydrochloric acid or polybasic acids such as maleic acid, fumaric acid, citric acid, and tartaric acid, and more preferable is maleic acid, from the viewpoint that the skin permeability of asenapine is further improved.

Moreover, a content of the asenapine and/or pharmaceutically acceptable salt in the adhesive agent layer according to the present invention cannot be generalized because it depends on the treatment target and purpose. Nevertheless, a total of a mass of the asenapine and a mass of the pharmaceutically acceptable salt in terms of free asenapine is preferably 1 to 15% by mass, more preferably 1.5 to 12% by mass, and further preferably 2 to 10% by mass, relative to the entire adhesive agent layer. If the content of the asenapine and/or pharmaceutically acceptable salt is less than the lower limit, the skin permeation amount tends to be decreased, so that the area of the patch needs to be increased. On the other hand, if the content exceeds the upper limit, a local adverse effect such as skin irritation tends to occur, or adhesive properties such as tackiness and adhesive force to skin tend to be decreased.

<Isopropyl Palmitate>

In the present invention, administering asenapine using a patch comprising isopropyl palmitate, the asenapine and/or pharmaceutically acceptable salt, an adhesive base agent to be described later, and, as necessary, sodium diacetate to be described later in combination in the adhesive agent layer makes it possible to achieve a therapeutically effective level of plasma concentration of asenapine which is sufficiently higher than ever achieved, and to sufficiently suppress the plasma concentration of an asenapine metabolite.

It should be noted that the isopropyl palmitate is known also as a transdermal absorption enhancer; however, even if, for example, propylene glycol or the like known as a transdermal absorption enhancer is used in place of the isopropyl palmitate according to the present invention, in combination with the asenapine and/or pharmaceutically acceptable salt, sodium diacetate, and adhesive base agent according to the present invention, it is difficult to achieve a therapeutically effective level of plasma concentration of asenapine which is sufficiently higher than ever achieved, and it is also difficult to sufficiently suppress the plasma concentration of an asenapine metabolite while achieving a sufficient level of plasma concentration of asenapine.

In the adhesive agent layer according to the present invention, a content of the isopropyl palmitate is preferably 2 to 15% by mass, more preferably 5 to 12% by mass, relative to the entire adhesive agent layer. If the content of the isopropyl palmitate is less than the lower limit, it tends to be difficult to achieve a therapeutically effective level of plasma concentration of asenapine which is sufficiently higher than ever achieved, and it tends to be difficult to sufficiently suppress the amount of an asenapine metabolite in plasma. On the other hand, if the content exceeds the upper limit, a local adverse effect such as skin irritation tends to occur.

Moreover, in the patch of the present invention, a mass ratio of the asenapine and/or pharmaceutically acceptable salt to the isopropyl palmitate, that is, a ratio of the total of the mass of the asenapine and the mass of the pharmaceutically acceptable salt in terms of free asenapine to a mass of the isopropyl palmitate (the mass of the asenapine and/or pharmaceutically acceptable salt in terms of free asenapine: the mass of the isopropyl palmitate) in the adhesive agent layer is preferably 1:0.1 to 1:10, more preferably 1:0.5 to 1:5. If the content of the isopropyl palmitate is less than the lower limit, it tends to be difficult to achieve a therapeutically effective level of plasma concentration of asenapine which is sufficiently higher than ever achieved, and it tends to be difficult to sufficiently suppress the amount of an asenapine metabolite in plasma. On the other hand, if the content exceeds the upper limit, a local adverse effect such as skin irritation tends to occur.

<Adhesive Base Agent>

The adhesive base agent according to the present invention is preferably a pressure-sensitive adhesive base agent. Examples of the pressure-sensitive adhesive base agent include (meth)acrylic ester (co)polymers, rubber-based adhesive agents, silicone polymers, polyurethane-based adhesive agents, and the like. One of these may be used alone, or two or more thereof may be used in combination.

The (meth)acrylic ester (co)polymers are (co)polymers containing acrylic ester and/or methacrylic ester as a main monomer unit(s) and, if necessary, a secondary monomer copolymerized therewith. Examples of the main monomer include methyl (meth)acrylate, ethyl (meth)acrylate, butyl (meth)acrylate, hexyl (meth)acrylate, heptyl (meth)acrylate, octyl (meth)acrylate, 2-ethylhexyl (meth)acrylate, and the like. One of these may be used alone, or two or more thereof may be used in combination. From the viewpoint that the adhesion of the patch becomes more excellent, 2-ethylhexyl (meth) acrylate is preferably used. Further, the secondary monomer is not particularly limited. Examples thereof include N-vinyl-2-pyrrolidone, methylvinyl pyrrolidone, (meth)acrylic acid, vinyl acetate, and the like.

Examples of the rubber-based adhesive agents include natural rubbers, polyisobutylene, alkyl vinyl ether (co)polymers, polyisoprene, polybutadiene, styrene-butadiene copolymers, styrene-isoprene copolymers, styrene-isoprene-styrene block copolymers, and the like. One of these may be used alone, or two or more thereof may be used in combination.

In the adhesive agent layer according to the present invention, the adhesive base agent is preferably at least one selected from the group consisting of styrene-isoprene-styrene block copolymers, (meth) acrylic ester (co)polymers, polyisobutylene, and silicone polymers, from the viewpoints that the adhesion and the skin permeability of a drug including asenapine tend to be further improved. More preferably, a styrene-isoprene-styrene block copolymer is used alone, or a styrene-isoprene-styrene block copolymer and polyisobutylene are used in combination.

The content of such an adhesive base agent is preferably such that a total content of the adhesive base agents is 10 to 90% by mass, more preferably 15 to 80% by mass, relative to the entire adhesive agent layer. If the content of the adhesive base agent is less than the lower limit, the adhesiveness of the patch to skin tends to be decreased. On the other hand, if the content exceeds the upper limit, the skin permeation amount of asenapine is decreased, so that it tends to be difficult to achieve a sufficient plasma concentration.

<Sodium Diacetate>

In the patch of the present invention, the adhesive agent layer preferably further comprises sodium diacetate. The sodium diacetate ($NaH(CH_3COO)_2$) may be a hydrate having crystallized water, but is preferably an anhydride from the viewpoint of the stability of the pharmaceutical preparation. In the present invention, by further incorporating sodium diacetate into the adhesive agent layer, an excellent effect of improving the skin permeability of asenapine is exhibited without using acetic acid and/or an alkali metal salt of acetic acid that have been conventionally used. In addition, since sodium diacetate is not as volatile as acetic acid, sodium diacetate is capable of exhibiting the effect of improving the skin permeability constantly over time.

Normally, the sodium diacetate can be obtained through crystallization after acetic acid and sodium acetate are mixed in water at a mole ratio (the number of moles of acetic acid:the number of moles of sodium acetate) of 1:1 and then the water is removed. Since the acetic acid and the sodium acetate are dissolved in water, mixing the two in water in this manner can obtain the sodium diacetate.

The sodium diacetate according to the present invention may be sodium diacetate obtained as described above. Nevertheless, from the viewpoint of suppressing reductions in performances of the patch, such as the production stability, the stability over time of the pharmaceutical preparation, and the skin permeability over time, the sodium diacetate is preferably synthesized by mixing the asenapine and/or pharmaceutically acceptable salt with sodium acetate. To be more specific, the sodium diacetate is preferably synthesized from sodium acetate whose particle diameter $D_{50}$ at a cumulative volume of 50% in a particle diameter distribution is 40 to 1000 μm, by mixing the asenapine or pharmaceutically acceptable salt with the sodium acetate in such a manner that the sodium acetate and the sodium diacetate synthesized from the sodium acetate have a particle diameter $D_{50}$ of 10 μm or smaller.

The average particle diameter of the asenapine and/or pharmaceutically acceptable salt used for such synthesis is not particularly limited, but is preferably 3 to 50 μm. Note that the average particle diameter of the asenapine or pharmaceutically acceptable salt can be obtained by an ordinary method in an image analysis using an optical microscope or measurement using a particle diameter distribution analyzer. In addition, in the case of employing the image analysis, the particle diameter means the maximum diameter in a cross section of a particle; in a case where a particle does not have a circular cross section, the particle diameter means a distance between two points on the border line of the cross section of the particle, the distance between the two points being selected such that the distance is the largest.

Meanwhile, the sodium acetate has to have a particle diameter $D_{50}$ of 40 to 1000 μm before mixing with the asenapine or pharmaceutically acceptable salt, where $D_{50}$ denotes a particle diameter at a cumulative volume of 50% in a particle diameter distribution. If the particle diameter $D_{50}$ of the sodium acetate is less than the lower limit, sodium diacetate cannot be synthesized sufficiently; moreover, an additional grinding step is required in some cases to make the particle diameter of the sodium acetate within the particle-diameter range, increasing the production cost. On the other hand, if the particle diameter $D_{50}$ exceeds the upper limit, the time required for the mixing and the product ion cost are increased, and sodium diacetate cannot be synthesized sufficiently. Further, such a particle diameter $D_{50}$ of the sodium acetate before mixing is particularly preferably 40 to 700 μm, and is preferably 10 to 1000'% larger than the particle diameter $D_{50}$ of the sodium acetate after mixing and sodium diacetate synthesized from the sodium acetate, from the viewpoint that sodium diacetate tends to be synthesized more efficiently and in a sufficient amount.

Such sodium acetate only needs to have a particle diameter within the above-described range, and ones generally marketed can be used as appropriate. Sodium acetate is normally marketed in the form of hydrous or anhydrous crystal, and any of the two may be used. Nevertheless, the number of crystallized water in the sodium acetate is preferably small, and anhydrous crystal is more preferable, from the viewpoint of preventing incidences such as crystal precipitation during the storage, color change, and a decrease in skin permeability when the sodium acetate is contained in the adhesive agent layer.

Note that the particle diameter distribution of such sodium acetate can be obtained by performing a measurement on a dispersion solution in which the sodium acetate is dispersed in ethyl acetate, the measurement performed according to a laser light scattering method (instrument used: laser light scattering particle diameter distribution analyzer (manufactured by Otsuka Electronics Co., Ltd., DLS-7000 model), Ar laser output: 75 mW).

A mixing ratio between the sodium acetate and the asenapine and/or pharmaceutically acceptable salt (the number of moles of the sodium acetate:a total number of moles of the asenapine and pharmaceutically acceptable salt) is preferably 1.5:1 to 6:1, more preferably 4:1. If the amount of the sodium acetate is less than the lower limit, there is not enough sodium acetate to be sodium diacetate, so that the amount of sodium diacetate obtained tends to be decreased. On the other hand, if the amount exceeds the upper limit, the amount of sodium diacetate synthesized tends to be decreased, and excessive sodium acetate tends to remain in the mixture.

The mixing is carried out in such a manner that the mixture is made to have a particle diameter $D_{50}$, that is, the particle diameter $D_{50}$ of the sodium acetate and/or the sodium diacetate synthesized from the sodium acetate, of 10 μm or smaller by the mixing. If the particle diameter $D_{50}$ exceeds the upper limit, sodium diacetate is not synthesized sufficiently. In the present invention, the particle diameter $D_{50}$ of the sodium acetate and the sodium diacetate is a particle diameter at a cumulative volume of 50% in a particle diameter distribution of a combination of the sodium acetate with the sodium diacetate. In a case where the sodium acetate does not remain due to the synthesis of the sodium diacetate, the particle diameter $D_{50}$ is a particle diameter at a cumulative volume of 50% in a particle diameter distribution of the sodium diacetate.

Such a particle diameter distribution can be obtained by measuring the particle diameter of an insoluble component in a dispersion solution which is obtained by adding a mixture obtained by mixing the sodium acetate with the asenapine and/or pharmaceutically acceptable salt into ethyl acetate, the measurement performed according to a laser light scattering method (instrument used: laser light scattering particle diameter distribution analyzer (manufactured by Otsuka Electronics Co., Ltd., DLS-7000 model), Ar laser output: 75 mW). Note that such a measurement method makes it possible to obtain the particle diameter $D_{50}$ in a particle diameter distribution of the mixture from which the asenapine and pharmaceutically acceptable salt are excluded, that is, the particle diameter $D_{50}$ of the sodium diacetate and the sodium acetate (if remaining) because asenapine and a pharmaceutically acceptable salt thereof are dissolved in ethyl acetate, so that the particle diameters of these are not reflected in the particle diameter distribution of the dispersion solution.

As the method for mixing the asenapine or pharmaceutically acceptable salt with the sodium acetate as described above, contact-mixing or grinding mixing is exemplified. The contact-mixing means mixing by which sodium acetate and asenapine or a pharmaceutically acceptable salt thereof are brought into contact with each other, receiving an impact from each other. The grinding mixing means mixing by which sodium acetate and asenapine or a pharmaceutically acceptable salt thereof receives an impact from each other while being ground.

Examples of the contact-mixing include methods in which the asenapine or pharmaceutically acceptable salt and the sodium acetate are placed in a vessel and mixed using a propeller mixer, a paddle mixer, an anchor mixer, a planetary mixer, a V blender (V-Shell), a Henschel mixer, or the like under low shear at a shear rate of approximately 1 to 1000 seconds$^{-1}$. Among these, a propeller mixer, a V blender, or a Henschel mixer is preferably used in the contact-mixing. Moreover, for example, in the case where the propeller mixer is used in such contact-mixing, it is preferable to perform mixing in such a manner as not to volatilize a solvent added as necessary, which will be described later, in a vessel having a capacity of 10 mL to 5000 L (the volume of the mixture: 10 mL to 5000 L), for a period of 30 to 120 minutes with the number of revolutions of 50 to 200 rpm.

Examples of the grinding mixing include methods in which the asenapine or pharmaceutically acceptable salt and the sodium acetate are placed in a vessel and mixed using a mortar and pestle mill, a rotary grinding mill, a ball mill, a rolling mill, a vibration mill, a buhrstone mill, a coffee mill-type mill, a homogenizer, a jet mill, or the like. Among these, a homogenizer is preferably used in the grinding mixing. In the case where such a homogenizer is used, it is preferable to perform mixing in such a manner as not to volatilize a solvent added as necessary, which will be described later, in a vessel having a capacity of 10 mL to 5000 L (the volume of the mixture: 10 mL to 5000 L) for 30 to 120 minutes.

In the contact-mixing and the grinding mixing, a solvent may be further added as necessary to the asenapine or pharmaceutically acceptable salt thereof and the sodium acetate. Examples of such a solvent include toluene, ethanol, methanol, ethyl acetate, and the like. One of these may be used alone, or two or more thereof may be used in combination. When the solvent is added, the amount added is preferably 50% by mass or less relative to the entire adhesive agent layer composition to be obtained, in consideration of the compatibility with the adhesive base agent, although the amount cannot be generalized because it depends also on the mixing method employed. Moreover, in the contact-mixing and the grinding mixing, a softener to be described later may be further added.

Such mixing makes it possible to synthesize the sodium diacetate according to the present invention from the sodium acetate. The resulting mixture contains the asenapine and/or pharmaceutically acceptable salt and the sodium diacetate, and may further contain the solvent and a residue of the sodium acetate used for the synthesis of the sodium diacetate.

In the present invention, whether sodium diacetate is synthesized can be checked by observing a decrease in a peak intensity derived from sodium acetate and an appearance of a peak derived from sodium diacetate in a measurement by an X-ray diffraction method (X ray: CuKα). In the present invention, from the viewpoint that the skin permeability of asenapine in the patch and the stability over time of the skin permeability are further improved, in measuring the obtained adhesive agent layer by the X-ray diffraction method, a peak intensity derived from the sodium diacetate is preferably higher than a peak intensity derived from the sodium acetate. Note that the sodium diacetate may be in a dissolved state.

In the adhesive agent layer according to the present invention, a content of the sodium diacetate is preferably 0.3 to 10% by mass, more preferably 0.5 to 6.0% by mass, relative to the entire adhesive agent layer. If the content of the sodium diacetate is less than the lower limit, the skin permeability of asenapine tends to be decreased. On the other hand, if the content exceeds the upper limit, a local adverse effect such as skin irritation tends to occur.

Note that in the case where the sodium diacetate is synthesized from the above-described sodium acetate, the content of the sodium diacetate in the adhesive agent layer can be obtained based on: the number of moles of the sodium acetate used as the raw material; and a peak ratio between a peak intensity derived from the sodium diacetate and a peak intensity derived from the sodium acetate, which are measured by an X-ray analysis performed on the obtained adhesive agent layer.

Moreover, in the patch of the present invention, a mole ratio of the asenapine and/or pharmaceutically acceptable salt to the sodium diacetate, that is, a ratio of the total number of moles of the asenapine and pharmaceutically acceptable salt to the number of moles of the sodium diacetate (the number of moles of the asenapine and/or pharmaceutically acceptable salt:the number of moles of the sodium diacetate) in the adhesive agent layer is preferably 1:0.5 to 1:4, more preferably 1:0.75 to 1:2. If the content of the sodium diacetate is less than the lower limit, the effect of improving the skin permeability of asenapine owing to the sodium diacetate added tends not to be exhibited sufficiently. On the other hand, if the content exceeds the upper limit, adhesive properties such as tackiness and adhesive force to skin tend to be decreased.

<Additive etc.>

The adhesive agent layer according to the present invention may further comprise, as necessary, additives such as a tackifier, a softener, a stabilizer, and an absorption enhancer, unless the effects of the present invention are not impaired.

Examples of the tackifier include alicyclic saturated hydrocarbon resins; rosin and rosin derivatives such as rosin glycerin ester, hydrogenated rosin, hydrogenated rosin glycerin ester, rosin pentaerythritol ester, and maleic rosin; terpene-based tackifier resins; petroleum-based tackifier resins; and the like. One of these may be used alone, or two or more thereof may be used in combination. In the present invention, petroleum-based tackifier resins are preferably used from the viewpoints of pharmaceutical physical properties such as cohesion and adhesion. In the case where the adhesive agent layer according to the present invention comprises such a tackifier, a mass ratio of the total content of the adhesive base agents to a content of the tackifier is (a total mass of the adhesive base agents:a mass of the tackifier) is preferably 1:6 to 1.5:1 (more preferably 1:5 to 1:1). If the content of the tackifier is less than the lower limit, the adhesive force to skin tends to be decreased. On the other hand, if the content exceeds the upper limit, the cohesive force of the adhesive agent layer tends to be decreased, and the pain during peeling off tends to be increased.

Examples of the softener include paraffin oils such as liquid paraffin; animal oils such as squalane and squalene; vegetable oils such as almond oil, olive oil, camellia oil, castor oil, tall oil, and peanut oil; silicone oils; liquid rubbers such as polybutene and polyisoprene; and the like. One of these may be used alone, or two or more thereof may be used in combination. In the present invention, from the viewpoints of pharmaceutical physical properties, liquid paraffin is preferably used. In the case where the adhesive agent layer according to the present invention comprises such a softener, a mass ratio of the total content of the adhesive base agents to a content of the softener (the total mass of the adhesive base agents:a mass of the softener) is preferably 1:6 to 5:1 (more preferably 1:4 to 3:1). If the content of the softener is less than the lower limit, the adhesive force to skin tends to be decreased. On the other hand, if the content exceeds the upper limit, the cohesive force of the adhesive agent layer tends to be decreased, and the adhesive agent layer or stickiness tends to remain on skin after peeling off.

Examples of the stabilizer that can be suitably used include tocopherol and ester derivatives thereof, ascorbic acid and ester derivatives thereof, dibutylhydroxytoluene, butylhydroxyanisole, and the like. One of these may be used alone, or two or more thereof may be used in combination. In the present invention, from the viewpoints of pharmaceutical physical properties, appearance, and drug-stabilizing effect, dibutylhydroxytoluene is more preferably used. In the case where the adhesive agent layer according to the present invention comprises such a stabilizer, a content thereof is preferably 0.1 to 3% by mass relative to the entire adhesive agent layer. If the content of the stabilizer is less than the lower limit, the stability of each component in the patch tends to be decreased. On the other hand, if the content exceeds the upper limit, the cohesive force of the adhesive agent layer tends to be decreased.

Examples of the absorption enhancer that can be suitably used include aliphatic alcohols such as isostearyl alcohol; fatty acids such as capric acid; fatty acid derivatives such as sorbitan monolaurate, propylene glycol monolaurate, isopropyl myristate, and lauric acid diethanolamide; glycols such as propylene glycol and polyethylene glycol; and the like. One of these may be used alone, or two or more thereof may be used in combination. Among these, sorbitan monolaurate and/or propylene glycol monolaurate are preferable from the viewpoint that the transdermal absorption of asenapine tends to be further improved. In the case where the adhesive agent layer according to the present invention comprises such an absorption enhancer, a content thereof is preferably 2 to 40% by mass relative to the entire adhesive agent layer. Further, in the case where the absorption enhancer is the propylene glycol monolaurate, a content thereof is more preferably 3 to 10% by mass relative to the entire resulting adhesive agent layer.

Moreover, in the case where the adhesive agent layer according to the present invention further comprises these additives, the total content is preferably 70% by mass or less relative to the entire adhesive agent layer.

Furthermore, the adhesive agent layer according to the present invention may further comprise acetic acid. However, in the present invention, preferably no acetic acid is added from the viewpoints that the skin permeability is kept sufficiently high for a long period, and that the irritation to skin is suppressed. In the present invention, particularly, in the case where the sodium diacetate is synthesized from the sodium acetate and incorporated, a patch having a sufficiently high skin permeability can be obtained without adding acetic acid, and it is possible to reduce the variation in the skin permeability of the drug among such pharmaceutical preparations.

In addition, the adhesive agent layer according to the present invention preferably comprises substantially no water. Since the adhesive agent layer according to the present invention is constituted mainly of hydrophobic components, if the water content exceeds 10% by mass, water is separated from the adhesive agent layer, so that the adhesion of the adhesive agent layer tends to be impaired. Here, the phrase comprises substantially no water means that no water is intentionally added at the time of production, and that the water content determined by a measurement according to the Karl Fischer's method based on The Japanese Pharmacopoeia is less than 10% relative to the entire adhesive agent layer.

In the patch of the present invention, incorporating a combination of the asenapine and/or pharmaceutically acceptable salt, the isopropyl palmitate, the adhesive base agent, and, as necessary, the sodium diacetate into the adhesive agent layer enables the skin permeability of asenapine to be sufficiently higher than ever achieved, and makes it possible to achieve a therapeutically effective level of plasma concentration of asenapine. Moreover, administering asenapine using such a patch can sufficiently suppress the plasma concentration of an asenapine metabolite.

According to the patch of the present invention, when a content of the asenapine and/or pharmaceutically acceptable salt in terms of free asenapine is 3.4 mg (a content of asenapine maleate: 4.8 mg) in the adhesive agent layer, an area under plasma concentration-time curve of the free asenapine between 2 and 120 hours for a period starting from the time when the patch is brought into contact with skin for 24 hours ($AUC_{2-120}$) can be 27,000 pg·hr/mL or more, more preferably 27,000 to 40,000 pg·hr/mL. Moreover, the patch of the present invention can make an $AUC_{2-120}$ of an asenapine metabolite in this period 20% or less, more preferably 16% or less, of the $AUC_{2-120}$ of the free asenapine.

The asenapine metabolite is a compound formed by metabolizing the asenapine and/or pharmaceutically acceptable salt. An example thereof includes N-desmethyl asenapine represented by the following formula (2):

[Chem. 2]

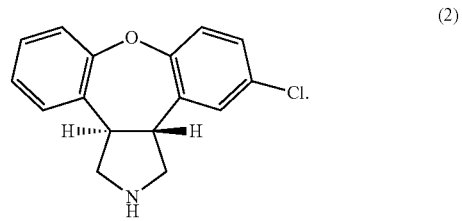

(2)

The N-desmethyl asenapine does not have a drug action (medical effect) as asenapine does. The N-desmethyl asenapine tends to cause adverse effects such as adverse effects on the cardiovascular system in comparison with asenapine. For example, in a case where 5 mg of asenapine maleate is orally administered (sublingual administration), the area under plasma concentration-time curve of the free asenapine for a period between 10 minutes and 72 hours ($AUC_{0.17-72}$) can be 25,000 to 38,000 pg·hr/mL. In this case, N-desmethyl asenapine has an $AUC_{0.17-72}$ of 10,000 to 17,000 pg·hr/mL, which is 40% or more of the $AUC_{0.17-120}$ of the free asenapine. In contrast, when approximately the same amount (4.8 mg) of asenapine is administered using the patch of the present invention, this makes it possible to sufficiently suppress the AUC of the asenapine metabolite while the free asenapine has an AUC equivalent to that in the case of the oral administration.

Note that, in the present invention, an area under plasma concentration-time curve (AUC) can be obtained specifically by the following method. First, 3.4 mg in mass of asenapine and/or a pharmaceutically acceptable salt thereof in terms of free asenapine, that is, a total of a mass of the asenapine and a mass of the pharmaceutically acceptable salt in terms of free asenapine, in a pharmaceutical preparation is administered once. The blood is collected at predetermined intervals for a predetermined period (in a case of a patch, a period between 2 hours and 120 hours after the patch is brought into contact with skin (the application period is 24 hours)) to measure amounts of the free asenapine and N-desmethyl asenapine in the plasma. Then, integrated values of plasma concentration-time curves obtained with the x axis representing time and the y axis representing plasma concentrations of the free asenapine and the N-desmethyl asenapine are calculated, so that AUCs can be obtained.

<Method for Producing Patch>

The patch of the present invention is not particularly limited, and can be produced by employing a known method for producing a patch as appropriate. For example, first, the asenapine and/or pharmaceutically acceptable salt, the isopropyl palmitate, the adhesive base agent, and, as necessary, the sodium diacetate, the additive, or the like are kneaded according to an ordinary method to thus obtain a homogeneous adhesive agent layer composition. Then, this adhesive agent layer composition is applied onto a surface (normally on one surface) of the support layer to a predetermined thickness, followed by, as necessary, heating and drying to remove a solvent, and the resultant is cut into a desired size, so that the patch of the present invention can be obtained.

The heating conditions can be selected as appropriate, depending on the solvent. The temperature condition is preferably normally 60 to 120° C., and the heating period is preferably normally 2 to 30 minutes.

In this event, in the case where the sodium diacetate used is synthesized from the above-described sodium acetate, the asenapine or pharmaceutically acceptable salt is mixed with the sodium acetate to obtain a mixture which contains the sodium diacetate and the asenapine or pharmaceutically acceptable salt, and the adhesive agent layer composition can be obtained by adding to the mixture the isopropyl palmitate, the adhesive base agent, and, as necessary, the additive or the like. Thus, the adhesive agent layer according to the present invention may further comprise a residue of the sodium acetate used for the synthesis of the sodium diacetate, the solvent, or the like, unless the effects of the present invention are not impaired. In the case the sodium acetate is contained, a content thereof is preferably 10% by mass or less relative to the entire adhesive agent layer from the viewpoint of preventing a decrease in the stability of the patch as a pharmaceutical preparation.

Moreover, the method for producing a patch of the present invention may further comprise a step of laminating the release liner to a surface of the adhesive agent layer, the surface being opposite to the support layer. In this case, first, the adhesive agent layer composition is applied onto one surface of the release liner to a predetermined thickness to form an adhesive agent layer. Then, the support layer is laminated to a surface of the adhesive agent layer, the surface being opposite to the release liner. The resultant is cut into a predetermined shape. In this way, the patch of the present invention may be obtained.

EXAMPLES

Hereinafter, the present invention will be more specifically described on the basis of Examples and Comparative Examples. However, the present invention is not limited to the following Examples. Note that, in each of Examples and Comparative Examples, particle diameter distribution determination, X-ray analysis, skin permeation test, and AUC measurement test were respectively conducted by methods illustrated below.

(Particle Diameter Distribution Determination)

First, sodium acetate used in each of Examples and Comparative Examples before mixing or a mixture obtained in each of Examples and Comparative Examples was added to ethyl acetate to disperse an insoluble component. Then, a particle diameter distribution curve was obtained by employing a laser light scattering method (instrument used: laser light scattering particle diameter distribution analyzer (manufactured by Otsuka Electronics Co., Ltd., DLS-7000 model), Ar laser output: 75 mW). Subsequently, from the obtained particle diameter distribution, each of a particle diameter $D_{10}$ (μm) at a cumulative volume of 10%, a particle diameter $D_{50}$ (μm) at a cumulative volume of 50%, a particle diameter $D_{90}$ (μm) at a cumulative volume of 90%, a volume-average particle diameter (μm), and a peak position were obtained.

(X-Ray Analysis)

First, an X-ray analysis was performed on sodium diacetate and sodium acetate as reference samples. An appropriate amount of sodium diacetate or sodium acetate was placed into a recess in a measurement glass plate, and the measurement surface was adjusted to be flat. Then, the measurement was performed by employing an apparatus and measurement conditions shown below:
apparatus: X'Pert-PRO (manufactured by Spectris Co., LTD.)
X ray: CuKα
scan angle: 5 to 50°
scan rate: 0.01°/min.

From the obtained spectra, peaks derived from the sodium diacetate were observed at three positions of $2\theta=11.1°$, 13.6°, and 22.3°; meanwhile, a peak derived from the sodium acetate was observed at one position of $2\theta=8.8°$.

Then, the support layer side of a patch obtained in each of Examples and Comparative Examples was fixed to a reflection-free plate with a double-sided adhesive tape. The release liner was removed therefrom, exposing the adhesive agent layer. Thereby, a measurement sample was prepared. An X-ray analysis was performed under the same conditions as above. From the obtained spectra, a total of peak intensities at the three positions ($2\theta$: 11.1°, 13.6°, 22.3°) was set as a peak intensity derived from sodium diacetate; meanwhile, a peak intensity at the one position ($2\theta$: 8.8°) was set as a peak intensity derived from sodium acetate.

(Skin Permeation Test)

First, a patch which had been cut into a 3-cm$^2$ circular shape and from which a release liner had been removed was applied to the corneum side of skin excised from a hairless mouse. Then, the skin was set to a flow-through diffusion cell kept at 32° C., so that the dermis side of the skin was located on the receptor chamber side. A phosphate buffer saline (32° C.) was introduced into the receptor chamber at a flow volume of approximately 3 ml per hour. Sample liquids were collected from the receptor chamber every 2 hours or 4 hours for 24 hours. Each of the collected sample liquids was quantified for the concentration of the drug (asenapine) by high-performance liquid chromatography. A skin permeation amount of asenapine was calculated according to the following formula:

skin permeation amount (μg/cm$^2$)=[drug concentration (μg/ml)×flow volume (ml)]/patch area (cm$^2$).

From this, a skin permeation amount per hour (skin permeation rate, Flux [μg/cm$^2$/hr]) was found. In addition, a cumulative skin permeation amount (μg/cm$^2$/24 hr) of the drug in 24 hours, that is, until 24 hours elapsed from the start of the measurement, was found. An availability ratio (%) of the drug was calculated according to the following formula:

availability ratio (%)={(cumulative skin permeation amount of the drug in 24 hours)/(drug content in 1 cm$^2$ of patch)}×100.

Note that it can be understood that a patch having a high skin permeation rate has a high skin permeability of the drug.

(AUC Measurement Test)

First, a patch (content in terms of free asenapine: 3.4 mg) which had been cut into 8 cm$^2$ and from which a release liner had been removed was applied to the upper arm of each of healthy adult men (18 people). The blood was collected every 4 hours for a period between 2 hours and 120 hours after the patch was applied. The amounts of free asenapine and N-desmethyl asenapine in the plasma were measured by high-performance liquid chromatography. Note that the patch was peeled off 24 hours after the application. Then, plasma concentration-time curves were created with the x axis representing time and the y axis representing plasma concentrations of the free asenapine and the N-desmethyl asenapine. Average values of integrated values between time 2 hours and 120 hours in the curves were calculated; thereby, an area under plasma concentration-time curve ($AUC_{2-120}$ [pg·hr/mL]) of each of the free asenapine and the N-desmethyl asenapine was obtained.

Example 1

First, 4.9 parts by mass of sodium acetate, 6 parts by mass of asenapine maleate (average particle diameter: 30 µm) (the number of moles of sodium acetate:the number of moles of asenapine maleate=4:1), and 29.1 parts by mass of liquid paraffin together with 10 parts by mass of toluene were placed into a 50-mL vessel, and subjected to contact-mixing at room temperature (25° C.) for 120 minutes using a propeller mixer at 200 rpm. Thereby, a mixture was obtained. Note that the particle diameter distributions of the sodium acetate before mixing and the obtained mixture in this case were measured. As a result, the sodium acetate before mixing had $D_{50}$ of 517.6 µm, and the mixture had a particle diameter $D_{50}$ of 6.93 µm.

Then, to this mixture, 5 parts by mass of isopropyl palmitate (IPP), 15 parts by mass of a styrene-isoprene-styrene block copolymer (SIS), 40 parts by mass of a petroleum-based tackifier resin (trade name: ARKON, manufactured by Arakawa Chemical Industries, Ltd.), and an appropriate amount of a solvent (toluene) were added and mixed together. Thus, a homogeneous adhesive agent layer composition was obtained.

Subsequently, this adhesive agent layer composition was applied onto one surface of a 75 µm-thick polyester film (release liner) having been subjected to a releasing process in such a manner that the thickness after drying was 100 µm. Toluene was removed by drying at 60° C. for 20 minutes. Thus, an adhesive agent layer was formed. Thereafter, a 25 µm-thick polyester film (support layer) was laminated on a surface of the adhesive agent layer, the surface being opposite to the release liner, followed by cutting to thus obtain a patch.

The X-ray analysis was performed on the obtained patch. As a result, only a peak derived from sodium diacetate was observed, and no peak derived from sodium acetate was observed. The content of the sodium diacetate in 100 parts by mass of the adhesive agent layer (the layer after toluene (solvent) was removed from the adhesive agent layer composition) in this case was 4.9 parts by mass (the number of moles of sodium diacetate:the number of moles of asenapine maleate=2:1). Table 1 shows the composition of the adhesive agent layer. Moreover, Table 1 also shows the amount of the sodium acetate added.

Example 2

A patch was obtained in the same manner as in Example 1, except that: the amount of asenapine maleate was 12 parts by mass, the amount of sodium acetate was 7.3 parts by mass (the number of moles of sodium acetate:the number of moles of asenapine maleate=3:1), and the amount of liquid paraffin was 20.7 parts by mass. Table 1 shows the composition of the adhesive agent layer in this case.

Example 3

A patch was obtained in the same manner as in Example 1, except that: the amount of asenapine maleate was 17 parts by mass, the amount of sodium acetate was 8.7 parts by mass (the number of moles of sodium acetate:the number of moles of asenapine maleate=2.5:1), and the amount of liquid paraffin was 14.3 parts by mass. Table 1 shows the composition of the adhesive agent layer in this case.

Comparative Example 1

A patch was obtained in the same manner as in Example 1, except that: isopropyl palmitate (IPP) was not used, and the amount of liquid paraffin was 34.1 parts by mass. Table 2 shows the composition of the adhesive agent layer in this case.

Comparative Examples 2 to 7

Patches were obtained in the same manner as in Example 1, except that: myristyl alcohol, oleic acid, propylene glycol, octyldodecanol, oleyl alcohol, and lauryl alcohol were respectively used in place of isopropyl palmitate (IPP). Table 2 shows the compositions of the adhesive agent layers in this case.

Figure 2:
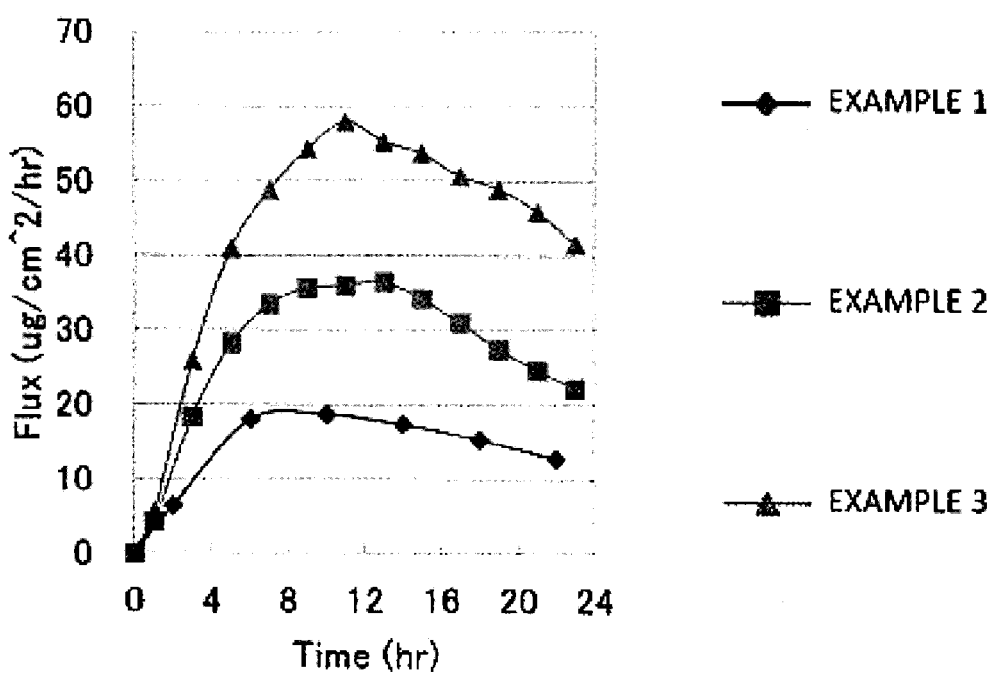
FIG. 2 is a graph showing a relation between the elapsed time from the application and skin permeation rates of asenapine in patches obtained in Examples 1 to 3.

The skin permeation test was conducted on the patch obtained in each of Examples and Comparative Examples. FIG. 1 shows a relation between the elapsed time from the application (Time [hr]) and the skin permeation rates of asenapine (Flux [µg/cm$^2$/hr]) in the patches obtained in Example 1 and Comparative Examples 1 to 7. FIG. 2 shows the relation regarding the patches obtained in Examples 1 to 3. Moreover, Tables 1 and 2 each show the maximum skin permeation rates [µg/cm$^2$/hr] and the availability ratios [%] of asenapine. Note that, in FIGS. 1 and 2, values of sample liquids collected every 2 hours or 4 hours (at 2, 4, 6, . . . 22, 24 hours; or at 4, 8, 12, . . . , 20, 24 hours) were plotted at every middle time point of the aforementioned time interval (at 1, 3, 5, . . . , 23 hours; or at 2, 6, 10, . . . , 22 hours).

Further, the AUC measurement test was conducted on the patch obtained in each of Examples and Comparative Examples. Table 1 shows the AUC ($AUC_{2-120}$ [pg·hr/mL]) of each of the asenapine and the asenapine metabolite in the patch obtained in Example 1. Additionally, Table 2 shows the AUC ($AUC_{2-120}$ [pg·hr/mL]) of the asenapine obtained by multiplying the AUC of the asenapine in Example 1 by a ratio of a value of the cumulative skin permeation amount of the drug in 24 hours obtained by the skin permeation test in each of Comparative Examples 1 to 7 to the value in Example 1.

Furthermore, in a case where the patch obtained in Example 1 was administered, the incidence proportion of adverse effects on the cardiovascular system in the AUC measurement test was 6%. Note that when 5 mg of asenapine maleate was orally administered (sublingual administration) to the healthy adult men (18 people), the average value of the area under plasma concentration-time curve of the free asenapine for a period between 10 minutes and 72 hours after the administration ($AUC_{0.17-72}$) was 32,074 pg·hr/mL, the average value of the $AUC_{0.17-72}$ of the N-desmethyl asenapine was 14,299 pg·hr/mL, and the incidence proportion of adverse effects on the cardiovascular system was 39%.

TABLE 1

|  | Example 1 | Example 2 | Example 3 |
|---|---|---|---|
| asenapine maleate [parts by mass] | 6 | 12 | 17 |
| (in terms of free form [parts by mass]) | (4.3) | (8.5) | (12.1) |

TABLE 1-continued

|  | Example 1 | Example 2 | Example 3 |
|---|---|---|---|
| sodium diacetate [parts by mass] | 4.9 | 7.3 | 8.7 |
| (amount of sodium acetate added [parts by mass]) | (4.9) | (7.3) | (8.7) |
| IPP [parts by mass] | 5 | 5 | 5 |
| SIS [parts by mass] | 15 | 15 | 15 |
| petroleum-based tackifier resin [parts by mass] | 40 | 40 | 40 |
| liquid paraffin [parts by mass] | 29.1 | 20.7 | 14.3 |
| total | 100 | 100 | 100 |
| maximum skin permeation rate [µg/hr/cm$^2$] | 18.6 | 36.4 | 57.9 |
| availability ratio [%] | 58.9 | 55.2 | 62.2 |
| asenapine AUC$_{2\text{-}120}$ [pg * hr/mL] | 33981 | — | — |
| asenapine metabolite AUC$_{2\text{-}120}$ [pg * hr/mL] | 5432 | — | — |

TABLE 2

|  | Comparative Example 1 | Comparative Example 2 | Comparative Example 3 | Comparative Example 4 | Comparative Example 5 | Comparative Example 6 | Comparative Example 7 |
|---|---|---|---|---|---|---|---|
| asenapine maleate [parts by mass] | 6 | 6 | 6 | 6 | 6 | 6 | 6 |
| (in terms of free form [parts by mass]) | (4.3) | (4.3) | (4.3) | (4.3) | (4.3) | (4.3) | (4.3) |
| sodium diacetate [parts by mass] | 4.9 | 4.9 | 4.9 | 4.9 | 4.9 | 4.9 | 4.9 |
| (amount of sodium acetate added [parts by mass]) | (4.9) | (4.9) | (4.9) | (4.9) | (4.9) | (4.9) | (4.9) |
| myristyl alcohol [parts by mass] | — | 5 | — | — | — | — | — |
| oleic acid [parts by mass] | — | — | 5 | — | — | — | — |
| propylene glycol [parts by mass] | — | — | — | 5 | — | — | — |
| octyldodecanol [parts by mass] | — | — | — | — | 5 | — | — |
| oleyl alcohol [parts by mass] | — | — | — | — | — | 5 | — |
| lauryl alcohol [parts by mass] | — | — | — | — | — | — | 5 |
| SIS [parts by mass] | 15 | 15 | 15 | 15 | 15 | 15 | 15 |
| petroleum-based tackifier resin [parts by mass] | 40 | 40 | 40 | 40 | 40 | 40 | 40 |
| liquid paraffin [parts by mass] | 34.1 | 29.1 | 29.1 | 29.1 | 29.1 | 29.1 | 29.1 |
| total | 100 | 100 | 100 | 100 | 100 | 100 | 100 |
| maximum skin permeation rate [µg/hr/cm$^2$] | 11.7 | 10.5 | 5.4 | 11.7 | 8.4 | 9.5 | 9.8 |
| availability ratio [%] | 36.7 | 27.4 | 14.0 | 29.5 | 23.7 | 26.3 | 28.2 |
| asenapine AUC$_{2\text{-}120}$ [pg*hr/mL] | 21173 | 15808 | 8077 | 17019 | 13673 | 15173 | 16269 |

As is apparent from the results shown in Tables 1 and 2 and FIGS. 1 and 2, it was verified that the patch of the present invention had a sufficient skin permeability of asenapine, and that it was possible to achieve a therapeutically effective level of plasma concentration of asenapine which is sufficiently higher than ever achieved. Moreover, it was verified that the patch of the present invention was capable of sufficiently suppressing the plasma concentration of the asenapine metabolite, and suppressing adverse effects.

INDUSTRIAL APPLICABILITY

As described above, the present invention makes it possible to provide a patch capable of achieving a therapeutically effective level of plasma concentration of asenapine which is sufficiently higher than ever achieved, and also capable of sufficiently suppressing the plasma concentration of an asenapine metabolite.

The invention claimed is:
1. A patch, comprising:
 a support layer; and
 an adhesive agent layer formed on the support layer and comprising isopropyl palmitate, an adhesive base agent, sodium diacetate, and at least one of asenapine and a pharmaceutically acceptable salt thereof,
 wherein a mass ratio of the asenapine and/or pharmaceutically acceptable salt in terms of free asenapine to the isopropyl palmitate in the adhesive agent layer is in a range of 1:0.1 to 1:5.
2. The patch according to claim 1, wherein a mass ratio of the asenapine and/or pharmaceutically acceptable salt in terms of free asenapine to the isopropyl palmitate in the adhesive agent layer is in a range of 1:0.41 to 1:5.
3. The patch according to claim 1, wherein a mole ratio of the asenapine and/or pharmaceutically acceptable salt to the sodium diacetate in the adhesive agent layer is in a range of 1:0.5 to 1:4.

4. The patch according to claim 1, wherein the adhesive base agent is at least one selected from the group consisting of a (meth)acrylic ester (co)polymer, a rubber-based adhesive agent, a silicone polymer, and a polyurethane-based adhesive agent.

5. The patch according to claim 1, wherein when a content of the asenapine and/or pharmaceutically acceptable salt in terms of free asenapine in the adhesive agent layer is 3.4 mg, an $AUC_{2-120}$ for a period starting from the time when the patch is brought into contact with skin for 24 hours is 27,000 pg·hr/mL or more, and an $AUC_{2-120}$ of an asenapine metabolite is 20% or less of the $AUC_{2-120}$ of the free asenapine.

6. The patch according to claim 2, wherein a mole ratio of the asenapine and/or pharmaceutically acceptable salt to the sodium diacetate in the adhesive agent layer is in a range of 1:0.5 to 1:4.

7. The patch according to claim 2, wherein the adhesive base agent is at least one selected from the group consisting of a (meth)acrylic ester (co)polymer, a rubber-based adhesive agent, a silicone polymer, and a polyurethane-based adhesive agent.

8. The patch according to claim 2, wherein when a content of the asenapine and/or pharmaceutically acceptable salt in terms of free asenapine in the adhesive agent layer is 3.4 mg, an $AUC_{2-120}$ of the free asenapine for a period starting from the time when the patch is brought into contact with skin for 24 hours is 27,000 pg·hr/mL or more, and an $AUC_{2-120}$ of an asenapine metabolite is 20% or less of the $AUC_{2-120}$ of the free asenapine.

9. The patch according to claim 3, wherein the adhesive base agent is at least one selected from the group consisting of a (meth)acrylic ester (co)polymer, a rubber-based adhesive agent, a silicone polymer, and a polyurethane-based adhesive agent.

10. The patch according to claim 3, wherein when a content of the asenapine and/or pharmaceutically acceptable salt in terms of free asenapine in the adhesive agent layer is 3.4 mg, an $AUC_{2-120}$ of the free asenapine for a period starting from the time when the patch is brought into contact with skin for 24 hours is 27,000 pg·hr/mL or more, and an $AUC_{2-120}$ of an asenapine metabolite is 20% or less of the $AUC_{2-120}$ of the free asenapine.

11. The patch according to claim 4, wherein when a content of the asenapine and/or pharmaceutically acceptable salt in terms of free asenapine in the adhesive agent layer is 3.4 mg, an $AUC_{2-120}$ of the free asenapine for a period starting from the time when the patch is brought into contact with skin for 24 hours is 27,000 pg·hr/mL or more, and an $AUC_{2-120}$ of an asenapine metabolite is 20% or less of the $AUC_{2-120}$ of the free asenapine.

12. The patch according to claim 7, wherein when a content of the asenapine and/or pharmaceutically acceptable salt in terms of free asenapine in the adhesive agent layer is 3.4 mg, an $AUC_{2-120}$ of the free asenapine for a period starting from the time when the patch is brought into contact with skin for 24 hours is 27,000 pg·hr/mL or more, and an $AUC_{2-120}$ of an asenapine metabolite is 20% or less of the $AUC_{2-120}$ of the free asenapine.

13. The patch according to claim 6, wherein the adhesive base agent is at least one selected from the group consisting of a (meth)acrylic ester (co)polymer, a rubber-based adhesive agent, a silicone polymer, and a polyurethane-based adhesive agent.

14. The patch according to claim 6, wherein when a content of the asenapine and/or pharmaceutically acceptable salt in terms of free asenapine in the adhesive agent layer is 3.4 mg, an $AUC_{2-120}$ of the free asenapine for a period starting from the time when the patch is brought into contact with skin for 24 hours is 27,000 pg·hr/mL or more, and an $AUC_{2-120}$ of an asenapine metabolite is 20% or less of the $AUC_{2-120}$ of the free asenapine.

15. The patch according to claim 13, wherein when a content of the asenapine and/or pharmaceutically acceptable salt in terms of free asenapine in the adhesive agent layer is 3.4 mg, an $AUC_{2-120}$ of the free asenapine for a period starting from the time when the patch is brought into contact with skin for 24 hours is 27,000 pg·hr/mL or more, and an $AUC_{2-120}$ of an asenapine metabolite is 20% or less of the $AUC_{2-120}$ of the free asenapine.

16. The patch according to claim 9, wherein when a content of the asenapine and/or pharmaceutically acceptable salt in terms of free asenapine in the adhesive agent layer is 3.4 mg, an $AUC_{2-120}$ of the free asenapine for a period starting from the time when the patch is brought into contact with skin for 24 hours is 27,000 pg·hr/mL or more, and an $AUC_{2-120}$ of an asenapine metabolite is 20% or less of the $AUC_{2-120}$ of the free asenapine.

17. The patch according to claim 3, wherein a mass ratio of the asenapine and/or pharmaceutically acceptable salt in terms of free asenapine to the isopropyl palmitate in the adhesive agent layer is in a range of 1:0.5 to 1:5.

* * * * *

UNITED STATES PATENT AND TRADEMARK OFFICE
CERTIFICATE OF CORRECTION

PATENT NO. : 9,687,474 B2  
APPLICATION NO. : 14/416964  
DATED : June 27, 2017  
INVENTOR(S) : Masayuki Suzuki et al.

Page 1 of 1

It is certified that error appears in the above-identified patent and that said Letters Patent is hereby corrected as shown below:

In the Claims

Column 19, Line 9, Claim 5:
Insert --of the free asenapine--, after "an $AUC_{2-120}$", and before "for a period starting from the time when the".

Signed and Sealed this
Eighteenth Day of September, 2018

Andrei Iancu
*Director of the United States Patent and Trademark Office*